US009833512B2

(12) United States Patent
Hoelzinger et al.

(10) Patent No.: US 9,833,512 B2
(45) Date of Patent: Dec. 5, 2017

(54) BLOCKING IL-9 SIGNALING IN CONJUNCTION WITH CHEMOTHERAPY TO TREAT CANCER (71) Applicants: Mayo Foundation for Medical Education and Research, Rochester, MN (US); Flory Mitrani, Scottsdale, AZ (US)

(72) Inventors: Dominique B. Hoelzinger, Phoenix, AZ (US); Sandra J. Gendler, Scottsdale, AZ (US); Peter A. Cohen, Scottsdale, AZ (US); Ana L. Dominguez, Scottsdale, AZ (US); Shannon E. Smith, Spring Valley, CA (US); Joseph Lustgarten, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 82 days.

(21) Appl. No.: 14/682,493

(22) Filed: Apr. 9, 2015

(65) Prior Publication Data
US 2015/0343057 A1  Dec. 3, 2015

Related U.S. Application Data (60) Provisional application No. 61/977,558, filed on Apr. 9, 2014.

(51) Int. Cl.
*A61K 39/395* (2006.01)
*C07K 16/24* (2006.01)
*A61K 45/06* (2006.01)
*A61K 39/00* (2006.01)

(52) U.S. Cl.
CPC ............ *A61K 45/06* (2013.01); *C07K 16/244* (2013.01); *A61K 2039/505* (2013.01)

(58) Field of Classification Search
CPC ................. A61K 2039/505; C07K 16/244
See application file for complete search history.

(56) References Cited

U.S. PATENT DOCUMENTS

| | | |
|---|---|---|
| 4,036,945 A | 7/1977 | Haber |
| 4,331,647 A | 5/1982 | Goldenberg |
| 6,645,486 B1 | 11/2003 | Van Snick et al. |
| 2007/0237763 A1 | 10/2007 | Banchereau et al. |
| 2010/0310501 A1 | 12/2010 | Boyman et al. |
| 2014/0186295 A1 | 7/2014 | Kupper et al. |

FOREIGN PATENT DOCUMENTS

WO   WO 9111465   8/1991

OTHER PUBLICATIONS

Cooper et al., "Production of Polyclonal Antisera," Unit 16.2, 8 pages, Copyright 1999.
Baines and Thorpe, "Purification of immunoglobulin g (IgG)," *Methods Mol Biol.*, vol. 10, Chpt. 8, pp. 79-104, 1992.
Barbas and Lerner, "Combinatorial immunoglobulin libraries on the surface of phage (Phabs): rapid selection of antigen-specific Fabs," *Methods*, 2(2):119-124, Apr. 1991.
Beatty et al., "CD40 agonists alter tumor stroma and show efficacy against pancreatic carcinoma in mice and humans," *Science*, 331(6024):1612-1616, Mar. 25, 2011.
Carlsson et al., "Molecular serum portraits in patients with primary breast cancer predict the development of distant metastases," *Proc Natl Acad Sci U S A.*, 108(34):14252-14257, Epub Aug. 15, 2011.
Carter et al., "Humanization of an anti-p185HER2 antibody for human cancer therapy," *Proc Natl Acad Sci U S A.*, 89(10):4285-4289, May 15, 1992.
Chen et al., "Autocrine/paracrine cytokine stimulation of leukemic cell proliferation in smoldering and chronic adult T-cell leukemia," *Blood*, 116(26):5948-5956, Epub Sep. 21, 2010.
Coligan et al., "Fragmentation of Immunoglobulin G" *Current Protocols in Immunology*, Unit 2.8, 10 pages, 1991.
Coligan et al., "Fragmentation of Immunoglobulin M" *Current Protocols in Immunology*, Unit 2.10A, 4 pages, 1991.
Coligan et al., "Peptides," *Current Protocols in Immunology*, Unit 9, 4 pages, 1993, [table of contents].
Coligan et al., "Production of Monoclonal Antibodies," *Current Protocols in Immunology*, Unit 2.5, 25 pages, 2006.
Coligan et al., "Production of Polyclonal Antisera," *Current Protocols in Immunology*, Unit 2.4, 9 pages, 1995.
Coligan et al., "Purification of Human IgA," *Current Protocols in Immunology*, Unit 2.10B, 7 pages, 1991.
Coligan et al., "Purification of Immunoglobulin G," *Current Protocols in Immunology*, Unit 2.7, 12 pages, 1991.
Coligan et al., "Purification of Immunoglobulin M," *Current Protocols in Immunology*, Unit 2.9, 3 pages, 1993.
Dall'Acqua et al., "Antibody humanization by framework shuffling," *Methods*, 36(1):43-60, May 2005.
Damschroder et al., "Framework shuffling of antibodies to reduce immunogenicity and manipulate functional and biophysical properties," *Mol Immunol.*, 44(11):3049-3060, Epub Jan. 22, 2007.
Dudley et al., "Adoptive cell transfer therapy following non-myeloablative but lymphodepleting chemotherapy for the treatment of patients with refractory metastatic melanoma," *J Clin Oncol.*, 23(10):2346-2357, Apr. 1, 2005.
Edelman et al., *Methods in Enzymology*, vol. 1, p. 422 (Academic Press 1967).
Eller et al., "IL-9 production by regulatory T cells recruits mast cells that are essential for regulatory T cell-induced immune suppression," *J Immunol.*, 186(1):83-91, Epub Nov. 29, 2010.
Elyaman et al., "IL-9 induces differentiation of TH17 cells and enhances function of FoxP3+ natural regulatory T cells," Proc Natl Acad Sci U S A., 106(31):12885-12890, Epub May 11, 2009.

(Continued)

Primary Examiner — Ruixiang Li
(74) Attorney, Agent, or Firm — Fish & Richardson P.C.

(57) ABSTRACT

This document provides methods and materials related to using inhibitors of IL-9 signaling in conjunction with chemotherapy to treat cancer (e.g., solid tumors). For example, methods and materials for using inhibitors of IL-9 signaling (e.g., anti-IL9 antibody preparations) in conjunction with chemotherapy to treat cancer (e.g., solid tumors such as breast cancer tumors or colon cancer tumors) or to reduce the growth rate of cancer (e.g., solid tumors such as breast cancer tumors or colon cancer tumors) within a mammal are provided.

5 Claims, 9 Drawing Sheets

(56) References Cited

OTHER PUBLICATIONS

Feng et al., "IL-9 contributes to immunosuppression mediated by regulatory T cells and mast cells in B-cell non-hodgkin's lymphoma," *J Clin Immunol.*, 31(6):1084-1094, Epub Sep. 4, 2011.

Gattinoni et al., "CTLA-4 dysregulation of self/tumor-reactive CD8+ T-cell function is CD4+ T-cell dependent," *Blood*, 108(12):3818-3823, Epub Aug. 1, 2006.

Goswami and Kaplan, "A brief history of IL-9," *J Immunol.*, 186(6):3283-3288, Mar. 15, 2011.

Green et al., "Antigen-specific human monoclonal antibodies from mice engineered with human Ig heavy and light chain YACs," *Nat Genet.*, 7(1):13-21, May 1994.

Green et al., "Production of Polyclonal Antisera," *Immunochemical Protocols* (Manson, ed.), vol. 10, pp. 1-5 (Humana Press 1992).

Griffiths et al., "Isolation of high affinity human antibodies directly from large synthetic repertoires," *EMBO J.*, 13(14):3245-3260, Jul. 15, 1994.

Harlow and Lane, "Index," *Antibodies: A laboratory manual*, p. 726, 1988.

Hoelzinger et al., "Abstract 3640: IL-9 is involved in the establishment of a tolerogenic milieu that prevents anti-tumor immunity," Proceedings of the 105th Annual Meeting of the American Association for Cancer Research, Apr. 5-9, 2014, San Diego, CA, *Cancer Res*, 74(19 Suppl), Oct. 1, 2014, 1 page.

Hoelzinger et al., "IL-9 strategy to perturb Treg function and enhance anti-tumor immunity (P4273)," AAI Immunology 2013 Annual Meeting, Honolulu, Hawaii, May 3-7, 2013, *J Immunol.*, 190 (Meeting Abstract Supplement) 140.9, May 2013, 1 page.

Hoelzinger et al., "Inhibition of adaptive immunity by IL9 can be disrupted to achieve rapid T-cell sensitization and rejection of progressive tumor challenges," *Cancer Res.*, 74(23):6845-6855, Epub Oct. 8, 2014.

Hornakova et al., "Acute lymphoblastic leukemia-associated JAK1 mutants activate the Janus kinase/STAT pathway via interleukin-9 receptor alpha homodimers," *J Biol Chem.*, 284(11):6773-6781, Epub Jan. 12, 2009.

Huse et al., "Generation of a large combinatorial library of the immunoglobulin repertoire in phage lambda," *Science*, 246(4935):1275-1281, Dec. 8, 1989.

Hwang et al., "Use of human germline genes in a CDR homology-based approach to antibody humanization," *Methods*, 36(1):35-42, May 2005.

Jabeen and Kaplan, "The symphony of the ninth: the development and function of Th9 cells," *Curr Opin Immunol.*, 24(3):303-307. Epub Feb. 22, 2012.

Jones et al., "Replacing the complementarity-determining regions in a human antibody with those from a mouse," *Nature*, 321(6069):522-525, Jun. 4-May 29, 1986.

Ju et al., "CP-690,550, a therapeutic agent, inhibits cytokine-mediated Jak3 activation and proliferation of T cells from patients with ATL and HAM/TSP," *Blood*, 117(6):1938-1946, Epub Nov. 24, 2010.

Kashmiri et al., "SDR grafting—a new approach to antibody humanization," *Methods*, 36(1):25-34, May 2005.

Khan et al., "Modulation of intestinal muscle contraction by interleukin-9 (IL-9) or IL-9 neutralization: correlation with worm expulsion in murine nematode infections," *Infect Immun.*, 71(5):2430-2438, May 2003.

Kim and Chung, "IL-9-producing invariant NKT cells protect against DSS-induced colitis in an IL-4-dependent manner," *Mucosal Immunol.*, 6(2):347-357, Epub Aug. 15, 2012.

Knappik et al., "Fully synthetic human combinatorial antibody libraries (HuCAL) based on modular consensus frameworks and CDRs randomized with trinucleotides," *J Mol Biol.*, 296(1):57-86, Feb. 11, 2000.

Ko et al., "Direct and differential suppression of myeloid-derived suppressor cell subsets by sunitinib is compartmentally constrained," *Cancer Res.*, 70(9):3526-3536, Epub Apr. 20, 2010.

Köhler and Milstein, "Continuous cultures of fused cells secreting antibody of predefined specificity," *Nature*, 256(5517):495-497, Aug. 7, 1975.

Lazar et al., "A molecular immunology approach to antibody humanization and functional optimization," *Mol Immunol.*, 44(8):1986-1998, Epub Oct. 31, 2006.

Leech and Grencis, "Induction of enhanced immunity to intestinal nematodes using IL-9-producing dendritic cells," *J Immunol.*, 176(4):2505-2511, Feb. 15, 2006.

Lemoli et al., "Interleukin-9 in human myeloid leukemia cells," *Leuk Lymphoma.*, 26(5-6):563-573, Aug. 1997.

Lemoli et al., "Interleukin-9 stimulates the proliferation of human myeloid leukemic cells," *Blood*, 87(9):3852-3859, May 1, 1996.

Lonberg et al., "Antigen-specific human antibodies from mice comprising four distinct genetic modifications," *Nature*, 368(6474):856-859, Apr. 28, 1994.

Losman et al., "Baboon anti-idiotype antibodies mimic a carcinoembryonic antigen epitope," *Int J Cancer.*, 46(2):310-314, Aug. 15, 1990.

Lu et al., "Mast cells are essential intermediaries in regulatory T-cell tolerance," *Nature,*.442(7106):997-1002, Epub Aug. 20, 2006.

Lu et al., "Th9 cells promote antitumor immune responses in vivo," *J Clin Invest.*, 122(11):4160-4171, Epub Oct. 15, 2012.

Lv and Wang, "The role of interleukin-9 in lymphoma," *Leuk Lymphoma.*, 54(7):1367-1372, Epub Dec. 5, 2012.

Lv et al., "Overexpression of IL-9 receptor in diffuse large B-cell lymphoma," *Int J Clin Exp Pathol.*, 6(5):911-916, Apr. 15, 2013.

Matsushita et al., "Frequent expression of interleukin-9 mRNA and infrequent involvement of interleukin-9 in proliferation of primary adult T-cell leukemia cells and HTLV-I infected T-cell lines," *Leuk Res.*, 21(3):211-216, Mar. 1997.

Merz et al., "Interleukin-9 expression in human malignant lymphomas: unique association with Hodgkin's disease and large cell anaplastic lymphoma," *Blood*, 78(5):1311-1317, Sep. 1, 1991.

Mitra et al., "Signal transducer and activator of transcription 5b (Stat5b) serine 193 is a novel cytokine-induced phospho-regulatory site that is constitutively activated in primary hematopoietic malignancies," *J Biol Chem.*, 287(20):16596-165608, Epub Mar. 22, 2012.

Nagato et al., "Expression of interleukin-9 in nasal natural killer/T-cell lymphoma cell lines and patients," *Clin Cancer Res.*, 11(23):8250-8257, Dec. 1, 2005.

Nisonoff et al., "Separation of univalent fragments from the bivalent rabbit antibody molecule by reduction of disulfide bonds," *Arch. Biochem. Biophys.*, 89:230-244, Aug. 1960.

Noelle and Nowak, "Cellular sources and immune functions of interleukin-9," *Nat Rev Immunol.*, 10(10):683-687, Epub Sep. 17, 2010.

Nowak and Noelle, "Interleukin-9 as a T helper type 17 cytokine," *Immunology*, 131(2):169-173, Oct. 2010.

Nowak et al., "IL-9 as a mediator of Th17-driven inflammatory disease," *J Exp Med.*, 206(8):1653-1660, Epub Jul. 13, 2009.

Oh et al., "A randomized, controlled trial to evaluate the effect of an anti-interleukin-9 monoclonal antibody in adults with uncontrolled asthma," *Respir Res.*, 14:93, Sep. 19, 2013.

Orlandi et al., "Cloning immunoglobulin variable domains for expression by the polymerase chain reaction," *Proc Natl Acad Sci U S A.*, 86(10):3833-3837, May 1989.

Pardoll, "The blockade of immune checkpoints in cancer immunotherapy," *Nat Rev Cancer.*, 12(4):252-264, Mar. 22, 2012.

Porter, "The hydrolysis of rabbit y-globulin and antibodies with crystalline papain," *Biochem J.*, 73:119-126, Sep. 1959.

Pulaski and Ostrand-Rosenberg, "Mouse 4T1 breast tumor model," *Curr Protoc Immunol.*, Chapter 20:Unit 20.2, 16 pages, May 2000.

Purwar et al., "Robust tumor immunity to melanoma mediated by interleukin-9-producing T cells," *Nat Med.*, 18(8):1248-1253, Epub Jul. 8, 2012.

Rader et al., "A phage display approach for rapid antibody humanization: designed combinatorial V gene libraries," *Proc Natl Acad Sci U S A.*, 95(15):8910-8915, Jul. 21, 1998.

Riechmann et al., "Reshaping human antibodies for therapy," *Nature*, 332(6162):323-327, Mar. 24, 1988.

(56) References Cited

OTHER PUBLICATIONS

Rosenberg et al., "Regression of established pulmonary metastases and subcutaneous tumor mediated by the systemic administration of high-dose recombinant interleukin 2," *J Exp Med.*, 161(5):1169-1188, May 1, 1985.

Rosenberg et al., "Treatment of 283 consecutive patients with metastatic melanoma or renal cell cancer using high-dose bolus interleukin 2," *JAMA*, 271(12):907-913, Mar. 23-30, 1994.

Rosok et al., "A combinatorial library strategy for the rapid humanization of anticarcinoma BR96 Fab," *J Biol Chem.*, 271(37):22611-22618, Sep. 13, 1996.

Rovero et al., "DNA vaccination against rat her-2/Neu p185 more effectively inhibits carcinogenesis than transplantable carcinomas in transgenic BALB/c mice," *J Immunol.*, 165(9):5133-5142, Nov. 1, 2000.

Sandhu, "Protein engineering of antibodies," *Crit Rev Biotechnol.*, 12(5-6):437-462, 1992.

Schmitt and Bopp, "Amazing IL-9: revealing a new function for an "old" cytokine," *J Clin Invest.*, 122(11):3857-3859, Epub Oct. 15, 2012.

Shang et al., "Aberrant activation of interleukin-9 receptor and downstream Stat3/5 in primary T-cell lymphomas in vivo in susceptible B6 and resistant C3H mice," *In Vivo.*, 22(6):713-720, Nov.-Dec. 2008.

Shang et al., "Interleukin-9 receptor gene is transcriptionally regulated by nucleolin in T-cell lymphoma cells," *Mol Carcinog.*, 51(8):619-627, Epub Aug. 1, 2011.

Shu et al., "Lymphocytes generated by in vivo priming and in vitro sensitization demonstrate therapeutic efficacy against a murine tumor that lacks apparent immunogenicity," *J Immunol.*, 143(2):740-748, Jul. 15, 1989.

Singer II et al., "Optimal humanization of 1B4, an anti-CD18 murine monoclonal antibody, is achieved by correct choice of human V-region framework sequences," *J Immunol.*, 150(7):2844-2857, Apr. 1, 1993.

Smith et al., "Signals through 4-1BB inhibit T regulatory cells by blocking IL-9 production enhancing antitumor responses," *Cancer Immunol Immunother.*, 60(12):1775-1787, Epub Jul. 26, 2011.

Stassen et al., "From interleukin-9 to T helper 9 cells," *Ann N Y Acad Sci.*, 1247:56-68, Epub Jan. 11, 2012.

Tan et al., "Antigen-specific Th9 cells exhibit uniqueness in their kinetics of cytokine production and short retention at the inflammatory site," *J Immunol.*, 185(11):6795-6801, Epub Oct. 22, 2010.

Taylor et al., "Human immunoglobulin transgenes undergo rearrangement, somatic mutation and class switching in mice that lack endogenous IgM," *Int Immunol.*, 6(4):579-591, Apr. 1994.

Townsend et al., "IL-9-deficient mice establish fundamental roles for IL-9 in pulmonary mastocytosis and goblet cell hyperplasia but not T cell development," *Immunity*, 13(4):573-583, Oct. 2000.

Turner et al., "IL-9-mediated survival of type 2 innate lymphoid cells promotes damage control in helminth-induced lung inflammation," *J Exp Med.*, 210(13):2951-2965, Epub Nov. 18, 2013.

Verhoeyen et al., "Reshaping human antibodies: grafting an antilysozyme activity," *Science*, 239(4847):1534-1536, Mar. 25, 1988.

Visekruna et al., "Tc9 cells, a new subset of CD8(+) T cells, support Th2-mediated airway inflammation," *Eur J Immunol.*, 43(3):606-618, Epub Jan. 31, 2013.

Wilhelm et al., "An IL-9 fate reporter demonstrates the induction of an innate IL-9 response in lung inflammation," *Nat Immunol.*, 12(11):1071-1077, Oct. 9, 2011.

Winter et al., "Making antibodies by phage display technology," *Annu Rev Immunol.*, 12:433-455, 1994.

Yang et al., "Mast cells mobilize myeloid-derived suppressor cells and Treg cells in tumor microenvironment via IL-17 pathway in murine hepatocarcinoma model," *PLoS One.*, 5(1):e8922, Jan. 27, 2010.

Ye et al., "Differentiation and immune regulation of IL-9-producing CD4+ T cells in malignant pleural effusion," *Am J Respir Crit Care Med.*, 186(11):1168-1179, Epub Oct. 11, 2012.

BLOCKING IL-9 SIGNALING IN CONJUNCTION WITH CHEMOTHERAPY TO TREAT CANCER

CROSS-REFERENCE TO RELATED APPLICATIONS

This application claims the benefit of U.S. Provisional Application Ser. No. 61/977,558, filed Apr. 9, 2014. The disclosure of the prior application is considered part of (and is incorporated by reference in) the disclosure of this application.

STATEMENT AS TO FEDERALLY SPONSORED RESEARCH

This invention was made with government support under CA155295 awarded by National Institutes of Health. The government has certain rights in the invention.

BACKGROUND

1. Technical Field

This document provides methods and materials related to using inhibitors of IL-9 signaling in conjunction with chemotherapy to treat cancer (e.g., solid tumors). For example, this document provides methods and materials for using inhibitors of IL-9 signaling (e.g., anti-IL9 antibody preparations) in conjunction with chemotherapy to treat cancer (e.g., solid tumors) or to reduce the growth rate of cancer (e.g., solid tumors) within a mammal.

2. Background Information

IL-9 is a paradoxical cytokine, as it mediates both pro-inflammatory events and tolerance induction. It is secreted by a host of pro-inflammatory immune cells including Th9 cells (Stassen et al., Ann. N Y Acad. Sci., 1247:56-68 (2012)), Th17 cells (Nowak and Noelle, Immunology, 131: 169-73 (2010), CD8$^+$ Tc9 cells (Visekruna et al., Eur. J. Immunol., 43:606-18 (2013)), eosinophils, mast cells, and innate lymphoid cells (Stassen et al., Ann. N YAcad. Sci., 1247:56-68 (2012), Goswami and Kaplan, J. Immunol., 186:3283-8 (2011), Jabeen and Kaplan, Curr. Opin. Immunol., 24:303-7 (2012), Noelle and Nowak, Nat. Rev. Immunol., 10:683-7 (2010), and Schmitt and Bopp, J. Clin. Invest., 122:3857-9 (2012)). It also is associated with tolerogenic cells such as T regulatory cells (Tregs). In this population IL-9 enhances Treg suppressive potency in an autocrine fashion (Elyaman et al., Proc. Natl. Acad. Sci. USA, 106:12885-90 (2009)), while promoting T cell tolerance via a paracrine impact upon mast cells (Eller et al., J. Immunol., 186:83-91 (2011), Lu et al., Nature, 442:997-1002 (2006), and Yang et al., PLoS ONE, 5:e8922 (2010)). This wide range of action is followed by an equally wide range of pathologies involving IL-9 secretion.

Most commonly IL-9 is linked to Th2 responses such as parasite expulsion and allergic airway inflammation, but it is also involved in autoimmunity and graft-versus-host disease (Noelle and Nowak, Nat. Rev. Immunol., 10:683-7 (2010)). IL-9 can be secreted by cells that promote opposite ends of the immune spectrum. For example: pro-inflammatory Th17 cells can produce IL-9 and exacerbate experimental autoimmune encephalitis (EAE) (Nowak et al., J. Exp. Med., 206:1653-60 (2009), whereas IL-9 secreted by Tregs renders them more suppressive and protects against EAE (Elyaman et al., Proc. Natl. Acad. Sci. USA, 106:12885-90 (2009)).

IL-9 also has seemingly contradictory roles in tumor biology. In some hematological tumors, the presence of IL-9 contributes to the establishment of a tolerogenic/immunosuppressive environment, or acts directly to drive tumor growth. IL-9 promotes the proliferation or survival of human lymphoid tumors such as Hodgkins lymphoma, acute lymphoblastic leukemia, myeloid leukemia, diffuse large B cell lymphoma, and NK T cell lymphoma (Merz et al., Blood, 78:1311-7 (1991), Lemoli et al., Blood, 87:3852-9 (1996), Lemoli et al., Leuk. Lymphoma, 26:563-73 (1997), Lv et al., Int. J. Clin. Exp. Pathol., 6:911-6 (2013), Lv and Wang, Leuk. Lymphoma, 54:1367-72 (2013) and Nagato et al., Clin. Cancer Res., 11:8250-7 (2005)). It also promotes the proliferation, migration and adhesion of human lung cancer cells (Matsushita et al., Leuk. Res., 21:211-6 (1997)).

IL-9, however, exhibits the opposite effect on melanoma biology in that it inhibits growth of B16 melanoma seeding in the lungs (Purwar et al., Nat. Med. 18:1248-53 (2012) and Lu et al., J. Clin. Invest., 122:4160-71 (2012)), through its effect directly on the lung epithelium, which then recruits dendritic cells.

SUMMARY

This document provides methods and materials related to using inhibitors of IL-9 signaling in conjunction with chemotherapy to treat cancer (e.g., solid tumors). For example, this document provides methods and materials for using inhibitors of IL-9 signaling (e.g., anti-IL9 antibody preparations) in conjunction with chemotherapy to treat cancer (e.g., solid tumors such as breast cancer tumors or colon cancer tumors) or to reduce the growth rate of cancer (e.g., solid tumors such as breast cancer tumors or colon cancer tumors) within a mammal. In some cases, inhibitors of IL-9 signaling (e.g., anti-IL9 antibody preparations) can be used alone or in conjunction with chemotherapy and/or anti-cancer immunotherapy to treat cancer (e.g., solid tumors) or to reduce the growth rate of cancer (e.g., solid tumors) within a mammal. For example, inhibitors of IL-9 signaling (e.g., an anti-IL-9 antibody preparation) can be used to treat a mammal suffering from breast cancer or colon cancer.

In general, one aspect of this document features a method for treating a mammal having colon or breast cancer. The method comprises, or consists essentially of, administering a chemotherapeutic agent and an anti-IL-9 or anti-IL-9 receptor antibody preparation to the mammal under conditions wherein the progression of the colon or breast cancer or the number of colon or breast cancer cells within the mammal is reduced. The mammal can be a human. The method can comprise administering the chemotherapeutic agent to the mammal before the preparation is administered to the mammal. The method can comprise administering the chemotherapeutic agent to the mammal at least one month before the preparation is administered to the mammal. The method can comprise administering the chemotherapeutic agent to the mammal at least two month before the preparation is administered to the mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials related to using inhibitors of IL-9 signaling in conjunction with chemotherapy to treat cancer (e.g., solid tumors). For example, this document provides methods and materials for using inhibitors of IL-9 signaling (e.g., anti-IL9 antibody preparations) in conjunction with chemotherapy to treat cancer (e.g., solid tumors such as breast cancer tumors or colon cancer tumors) or to reduce the growth rate of cancer (e.g., solid tumors such as breast cancer tumors or colon cancer tumors) within a mammal Examples of inhibitors of IL-9 signaling include, without limitation, anti-IL9 antibodies, anti-IL-9 receptor antibodies, siRNA molecules against IL-9, and siRNA molecules against an IL-9 receptor.

The term "antibody" as used herein refers to intact antibodies as well as antibody fragments that retain some ability to bind an epitope. Such fragments include, without limitation, Fab, F(ab')$_2$, and Fv antibody fragments. The term "epitope" refers to an antigenic determinant on an antigen to which the paratope of an antibody binds. Epitopic determinants usually consist of chemically active surface groupings of molecules (e.g., amino acid or sugar residues) and usually have specific three dimensional structural characteristics as well as specific charge characteristics.

The antibodies provided herein can be any antibody (e.g., a monoclonal antibody) having binding affinity (e.g., specific binding affinity) for IL-9 or an IL-9 receptor. For example, an anti-IL-9 antibody preparation or an anti-IL-9 receptor antibody preparation provided herein can be a preparation of Fab fragments having the ability to bind to IL-9 (e.g., human IL-9) or IL-9 receptor (e.g., a human IL-9 receptor). Any appropriate method can be used to produce Fab fragments from intact antibodies. For example, standard papain digestion methods can be used to make a Fab antibody preparation.

Antibodies provided herein can be prepared using any appropriate method. For example, a sample containing a human IL-9 polypeptide or human IL-9 receptor polypeptide can be used as an immunogen to elicit an immune response in an animal such that specific antibodies are produced. The immunogen used to immunize an animal can be chemically synthesized or derived from translated cDNA. In some cases, the immunogen can be conjugated to a carrier polypeptide, if desired. Commonly used carriers that are chemically coupled to an immunizing polypeptide include, without limitation, keyhole limpet hemocyanin (KLH), thyroglobulin, bovine serum albumin (BSA), and tetanus toxoid.

The preparation of polyclonal antibodies is well-known to those skilled in the art. See, e.g., Green et al., Production of Polyclonal Antisera, in IMMUNOCHEMICAL PROTOCOLS (Manson, ed.), pages 1 5 (Humana Press 1992) and Coligan et al., Production of Polyclonal Antisera in Rabbits, Rats, Mice and Hamsters, in CURRENT PROTOCOLS IN IMMUNOLOGY, section 2.4.1 (1992). In addition, those of skill in the art will know of various techniques common in the immunology arts for purification and concentration of polyclonal antibodies, as well as monoclonal antibodies (Coligan, et al., Unit 9, Current Protocols in Immunology, Wiley Interscience, 1994).

The preparation of monoclonal antibodies also is well-known to those skilled in the art. See, e.g., Kohler & Milstein, *Nature* 256:495 (1975); Coligan et al., sections 2.5.1 2.6.7; and Harlow et al., ANTIBODIES: A LABORATORY MANUAL, page 726 (Cold Spring Harbor Pub. 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein A Sepharose, size exclusion chromatography, and ion exchange chromatography. See, e.g., Coligan et al., sections 2.7.1 2.7.12 and sections 2.9.1 2.9.3; Barnes et al., Purification of Immunoglobulin G (IgG), in METHODS IN MOLECULAR BIOLOGY, VOL. 10, pages 79 104 (Humana Press 1992).

In addition, methods of in vitro and in vivo multiplication of monoclonal antibodies are well known to those skilled in the art. Multiplication in vitro can be carried out in suitable culture media such as Dulbecco's Modified Eagle Medium or RPMI 1640 medium, optionally replenished by mammalian serum such as fetal calf serum, or trace elements and growth sustaining supplements such as normal mouse peritoneal exudate cells, spleen cells, and bone marrow macrophages. Production in vitro provides relatively pure antibody preparations and allows scale up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells (e.g., osyngeneic mice) to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

In some cases, the antibodies provided herein can be made using non-human primates. General techniques for raising therapeutically useful antibodies in baboons can be found, for example, in Goldenberg et al., International Patent Publication WO 91/11465 (1991) and Losman et al., *Int. J. Cancer,* 46:310 (1990).

In some cases, the antibodies can be humanized monoclonal antibodies. Humanized monoclonal antibodies can be produced by transferring mouse complementarity determining regions (CDRs) from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions when treating humans. General techniques for cloning murine immunoglobulin variable domains are described, for example, by Orlandi et al., *Proc. Nat'l. Acad. Sci. USA* 86:3833 (1989). Techniques for producing humanized monoclonal antibodies are described, for example, by Jones et al., *Nature* 321:522 (1986); Riechmann et al., *Nature* 332:323 (1988); Verhoeyen et al., *Science* 239:1534 (1988); Carter et al., *Proc. Nat'l. Acad. Sci. USA* 89:4285 (1992); and Sandhu, *Crit. Rev. Biotech.* 12:437 (1992); Singer et al., *J. Immunol.* 150:2844 (1993). In some cases, humanization such as super humanization can be used as described elsewhere (Hwang et al., *Methods,* 36:35-42 (2005)). In some cases, SDR grafting (Kashmiri et al., *Methods,* 36:25-34 (2005)), human string content optimization (Lazar et al., *Mol. Immunol.,* 44:1986-1998 (2007)), framework shuffling (Dall'Acqua et al., *Methods,* 36:43-60 (2005); and Damschroder et al., *Mol. Immunol.,* 44:3049-3060 (2007)), and phage display approaches (Rosok et al., *J. Biol. Chem.,* 271:22611-22618 (1996); Radar et al., *Proc. Natl Acad. Sci. USA,* 95:8910-8915 (1998); and Huse et al., *Science,* 246:1275-1281 (1989)) can be used to obtain anti-IL-9 or anti-IL-9 receptor antibody preparations. In some cases, fully human antibodies can be generated from recombinant human antibody library screening techniques as described elsewhere (Griffiths et al., *EMBO J.,* 13:3245-3260 (1994); and Knappik et al., *J. Mol. Biol.,* 296:57-86 (2000)).

Antibodies provided herein can be derived from human antibody fragments isolated from a combinatorial immunoglobulin library. See, for example, Barbas et al., METHODS: A COMPANION TO METHODS IN ENZYMOL- OGY, VOL. 2, page 119 (1991) and Winter et al., *Ann. Rev. Immunol.* 12: 433 (1994). Cloning and expression vectors that are useful for producing a human immunoglobulin phage library can be obtained, for example, from STRATA-GENE Cloning Systems (La Jolla, Calif.).

In addition, antibodies provided herein can be derived from a human monoclonal antibody. Such antibodies can be obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody secreting hybridomas. Methods for obtaining human antibodies from transgenic mice are described by Green et al. (*Nature Genet.*, 7:13 (1994)), Lonberg et al. (*Nature*, 368:856 (1994)), and Taylor et al. (*Int. Immunol.*, 6:579 (1994)).

Antibody fragments can be prepared by proteolytic hydrolysis of an intact antibody or by the expression of a nucleic acid encoding the fragment. Antibody fragments can be obtained by pepsin or papain digestion of intact antibodies by conventional methods. For example, Fab fragments can be produced by enzymatic cleavage of antibodies with papain. In some cases, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. In some cases, an enzymatic cleavage using pepsin can be used to produce two monovalent Fab' fragments and an Fc fragment directly. These methods are described, for example, by Goldenberg (U.S. Pat. Nos. 4,036,945 and 4,331,647). See also Nisonhoff et al., *Arch. Biochem. Biophys.* 89:230 (1960); Porter, *Biochem. J.* 73:119 (1959); Edelman et al., METHODS IN ENZYMOLOGY, VOL. 1, page 422 (Academic Press 1967); and Coligan et al. at sections 2.8.1 2.8.10 and 2.10.1 2.10.4.

Other methods of cleaving antibodies, such as separation of heavy chains to form monovalent light heavy chain fragments, further cleavage of fragments, or other enzymatic, chemical, or genetic techniques may also be used provided the fragments retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acid with which it is naturally associated. Thus, a substantially pure antibody is any antibody that is removed from its natural environment and is at least 60 percent pure. A substantially pure antibody can be at least about 65, 70, 75, 80, 85, 90, 95, or 99 percent pure.

As described herein, inhibitors of IL-9 signaling (e.g., anti-IL9 antibody preparations) can be used in conjunction with chemotherapy to treat cancer or to reduce the growth rate of cancer within a mammal. For example, at least one inhibitor of IL-9 signaling can be administered to a mammal with breast or colon cancer before, together with, or following the administration of at least one chemotherapeutic agent. Examples of cancers that can be treated using a combination of at least one inhibitor of IL-9 signaling and at least one chemotherapeutic agent include, without limitation, breast cancers and colon cancers. Examples of chemotherapeutic agents that can be used in combination with at least one inhibitor of IL-9 signaling to treat cancer or to reduce the growth rate of cancer within a mammal as described herein include, without limitation, anti-PD-1, anti-PD-L1, anti-CTLA4, Herceptin® (trastuzumab), cyclophosphamide, gemcitabine, capecitabine, azacytadine, bortezomib, carboplatin, cisplatin, etoposide, imatinib,5-fluorouracil/leucovorin, docetaxel, paclitaxel, nab-paclitaxel, irinotecan, doxorubicin, methotrexate, and oxaliplatin therapies.

In some cases, inhibitors of IL-9 signaling (e.g., anti-IL9 antibody preparations) can be used alone or in conjunction with at least one chemotherapeutic agent and/or at least one anti-cancer immunotherapeutic agent to treat cancer (e.g., solid tumors) or to reduce the growth rate of cancer (e.g., solid tumors) within a mammal. For example, at least one inhibitor of IL-9 signaling can be administered to a mammal with breast or colon cancer before, together with, or following the administration of at least one anti-cancer immunotherapeutic agent. Examples of anti-cancer immunotherapeutic agents that can be used in combination with at least one inhibitor of IL-9 signaling to treat cancer or to reduce the growth rate of cancer within a mammal as described herein include, without limitation, anti-cancer vaccines.

The invention will be further described in the following examples, which do not limit the scope of the invention described in the claims.

EXAMPLES

Example 1

Inhibition of Adaptive Immunity by IL-9 can be Disrupted to Achieve Rapid T Cell Sensitization and Rejection of Progressive Tumor Challenges Mice, Cell Lines, and Reagents BALB/c mice were purchased from NCI (Fredrick, Md.), and IL-9ko mice were obtained from Andrew McKenzie (MRC, Laboratory of Molecular Biology, Cambridge, UK). They were housed under specific pathogen-free conditions. TUBO cells are derivatives of a spontaneous mammary carcinoma in WT mice and were obtained from Dr. Forni (Torino, Italy). 4T1 are a mammary carcinoma line derived from 410.4 mammary tumors. BM 185 cells were derived from bone marrow from an acute lymphoblastic leukemia model, originally provided by D. Kohn (University of Southern California, Los Angeles). All were maintained in complete RPMI 1640 medium supplemented with 10% FCS, 2 mM glutamine, $5\times10^{-5}$ M 2-ME, and 50 µg/ml gentamicin.

Anti-IL-9 mAb (MM9C1) and its isotype control Ab were obtained from Dr. Jacques Van Snick (Ludwig Institute, Brussels, Belgium). Depleting antibodies were obtained as follows: anti-CD4 (clone GK 1.5, BioLegend), anti-CD8α (clone 2.43, LifeSpan BioSciences) antibodies or the corresponding rat IgG isotype control. CD4$^+$ and CD8$^+$ T cells were enriched using negative selection kits (Invitrogen, Carlsbad, Calif.).

In Vivo Tumor Studies

WT and IL-9ko mice were implanted subcutaneously (s.c.) with $1\times10^6$ TUBO, or $1\times10^6$ 4T1, measured twice weekly and sacrificed when the tumors reached 1 cm$^2$ or showed signs of external necrosis. Tumor volume was calculated using two perpendicular measurements in the following formula: [a$^2$×b/2]. For CD4$^+$ and CD8+ T cell depletion experiments, anti-CD4 and -CD8 antibodies and the corresponding isotype control were delivered i.p. at 125

μg each. Mice were pretreated 3-4 days before tumor inoculation, and then subsequently once weekly for 4 weeks. For IL-9 neutralization experiments, WT mice were injected s.c. with $2.5 \times 10^4$ 4T1cells and anti-IL-9, isotype control Ab (100 μg each) or left untreated. Abs were delivered to WT and IL-9ko mice through intra-peritoneal (i.p.) injections three times per week for 3 weeks.

ELISpot Assays $1 \times 10^5$ 4T1 splenocytes were co cultured with either $5 \times 10^4$ 4T1 or TUBO cells. $5 \times 10^4$ 4T1 lymphocytes were co cultured with either $2.5 \times 10^4$ 4T1 or TUBO cells, following the manufacturers' instructions. $CD4^+$ and $CD8^+$ T cells were enriched from the spleens of naïve and 4T1-bearing WT and IL-9ko mice using a negative isolation kit (Invitrogen, Carlsbad Calif.). $1 \times 10^5$ T cells were co-cultured with $2.5 \times 10^4$ 4T1 cells or with BM185, a non-specific control tumor line for 40 hours. Each experimental condition was executed in biological triplicates, which in turn comprised triplicate wells. Manufacturer's instructions were followed to reveal INFγ positive spots using the interferon gamma ELISpot kit from Mabtech (cat #3321-2HW-Plus). The plates were imaged and evaluated by ZellNet Consulting, Inc. (Fort Lee N.J.), and result expressed as average of triplicate spots per condition. Phorbol 12-myristate 13-acetate (PMA) was used as a positive control of cell activation.

Immunohistochemistry

4T1 tumors were harvested from IL-9ko and WT mice, formalin fixed, and paraffin embedded. Four micron sections were incubated overnight with or without anti-CD8 alpha antibody (Thermo scientific, MA5-16761) overnight, followed by detection using ImmPRESS™ Reagent Anti Rat IgG, peroxidase (Vector Labs MP-7404) followed by DAB substrate kit (Vector labs SK-4100). Slides were mounted in Permount and visualized with a Leica DMRB microscope. Images were acquired at a magnification of 200× with a numerical aperture of 2, at room temperature with an Olympus DP71 camera using the DPController software (Olympus).

Winn Assays

Total splenocytes were harvested from 4T1 bearing WT, and from IL-9ko mice that had rejected $1 \times 10^6$ 4T1 cells 2-3 months prior, and which were rechallenged with $5 \times 10^5$ 4T1 cells one week before the start of the assay. Splenocytes were mixed with $2.5 \times 10^4$ 4T1 cells and co-injected s.c. into WT mice in the following proportions of splenocytes to 4T1 cells: 100:1, 33:1 and only 4T1. Mice were monitored twice a week for tumor growth and tumor growth was compared to that of 4T1 cells mixed with splenocytes derived from tumor bearing WT. A repeat experiment was done using negatively enriched $CD8^+$ T from tumor bearing and naïve WT and IL-9ko mice, cells were co-injected with 4T1 cells at a concentration of 25:1 ($CD8^+$ T cells:4T1 cells). Each experimental cohort consisted of T cells isolated from three individual mice, and each individual isolate was injected in duplicate, bringing the total per condition to six.

Statistical Analyses

Statistical significance of data was determined in most cases using the Student's t-test to evaluate the p value. The log-rank (Mantel-Cox) test was used to evaluate significant differences in survival. For the comparison of differences in growth curves, the tumor size was compared over days 9, 12, and 15 between groups using repeated measures analysis of variance.

Figure 1A:
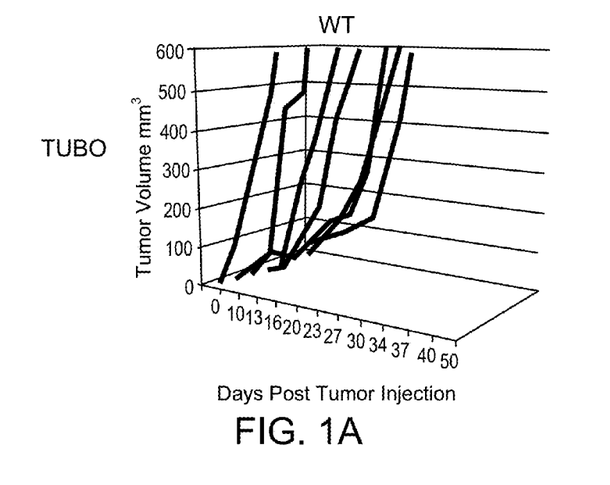
FIGS. 1A-I. TUBO and 4T1 mammary carcinomas are rejected in IL-9ko mice. Growth of $1 \times 10^6$ TUBO cells implanted s.c. in the flank of (A) WT and (B) IL-9ko mice. (C) Survival plot of TUBO bearing mice, showing 100% of IL-9ko mice surviving after day 85 post tumor injection (p<0.0001). Growth of $1 \times 10^6$ 4T1 cells implanted s.c. in the flank of (D) WT and (E) IL-9ko mice. (F) Survival plot of 4T1 bearing mice, showing 75% of IL-9ko mice surviving after day 50 post tumor injection (p<0.0001). Growth of $1 \times 10^5$ CT26 cells implanted s.c. in the flank of (G) WT and (H) IL-9ko mice. (I) Survival plot of CT26 bearing mice, showing 75% of IL-9ko mice surviving after day 50 post tumor injection (p<0.001). Arrows denote the day of rechallenge with $1 \times 10^6$ TUBO or 4T1 cells (7 and 8 IL-9ko mice respectively). Data are cumulative of a minimum of 2 experiments.
Figure 1B:
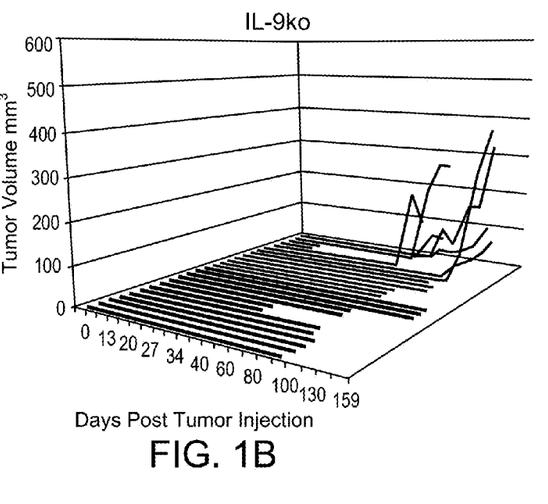
Figure 1C:
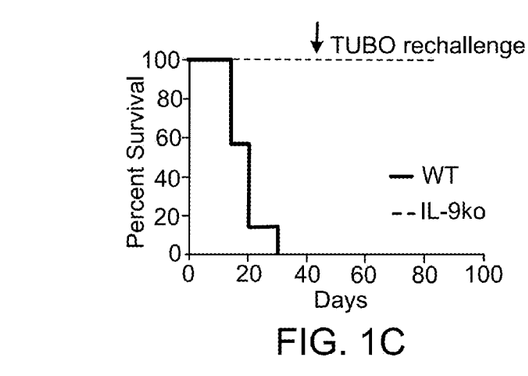

Mammary Carcinomas TUBO and 4T1, as Well as Colon Caracinoma CT26 are Rejected in IL-9Ko Mice IL-9ko mice were used to investigate the role of IL-9 in inhibiting anti-tumor immune activity. Subcutaneous (s.c.) injection of TUBO cells in the flank of BALB/c (WT) mice resulted in robust tumor growth within 10 days after tumor delivery (n=7, FIG. 1A). Similar s.c. tumor inoculations in IL-9ko mice had a markedly different effect: tumors were rejected in 78% of the IL-9ko mice (21/27 mice) (FIG. 1B). In the 6 mice that developed tumors, the average onset of macroscopic tumor growth was delayed to 60 days (FIG. 1B, p=0.0001). In addition to significantly delayed tumor onset, slower growth was observed in IL-9ko mice, resulting in 100% survival 85 days after tumor delivery, compared to 0% survival at day 30 in the WT control group (FIG. 1C, p<0.0001). To confirm that tumor rejection was based on an immune component and not due to a systemic effect linked to IL-9 deficiency, the TUBO challenge was repeated in 7 of the IL-9ko mice that rejected TUBO two months after the initial challenge (FIG. 1C, arrow). All the mice failed to develop tumors, suggesting that these rechallenged mice developed a memory response to TUBO cells.

Figure 1D:
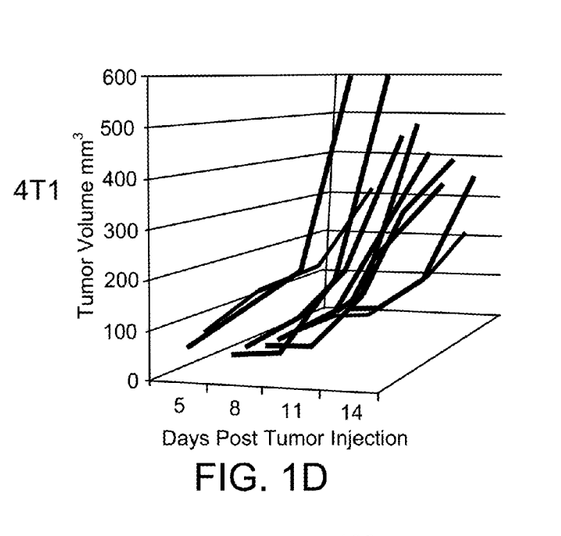
Figure 1E:
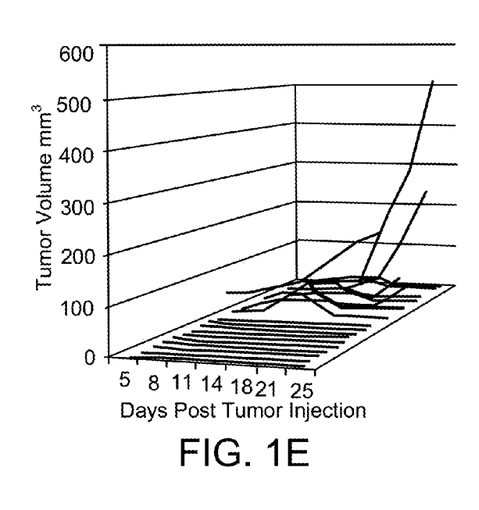
Figure 1F:
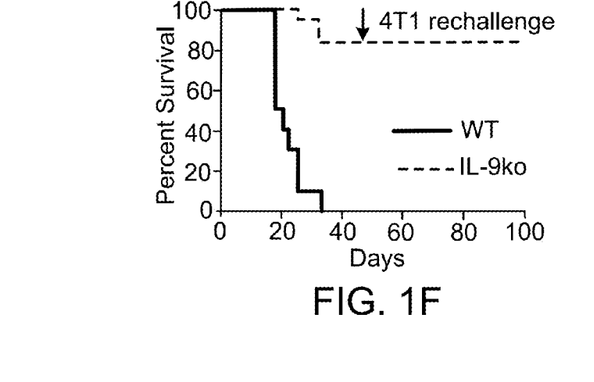

This experiment was repeated with 4T1 cells, and palpable tumors were detected 5 days post injection, which grew exponentially in WT mice (n=10, FIG. 1D). In contrast, 68% (15/22) of IL-9ko mice failed to develop or rejected tumors (FIG. 1E). Of the remaining 32% (7/22) of IL-9ko mice that developed tumors, tumor growth was significantly slower compared to WT mice, and 75% of the IL-9ko mice survived past day 50 post tumor inoculation (FIG. 1F, p<0.0001). To confirm that 4T1 rejection also elicited a memory response, 8 of the IL-9ko mice that rejected 4T1 were rechallenged with 4T1 (FIG. 1F, arrow). As before, all the mice failed to develop tumors, suggesting the existence of a memory response to 4T1 cells. None of the IL-9ko mice in which original 4T1 tumors progressed exhibited any evidence of macrometastasis in the lungs, liver or spleen (evaluated 80-100 days post injection), which is routinely observed in WT mice.

Figure 1G:
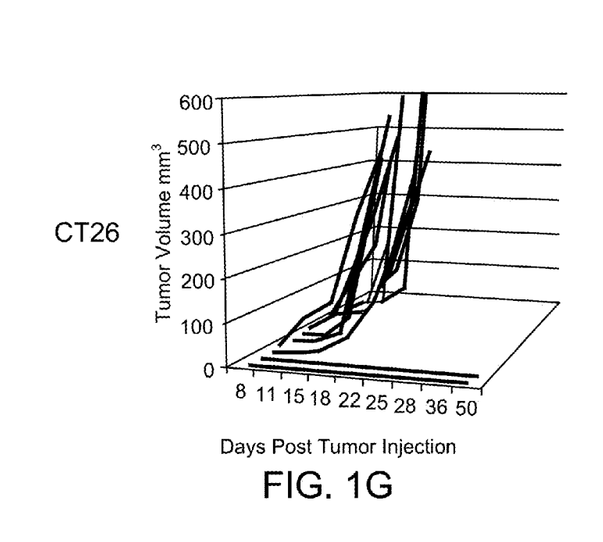
Figure 1H:
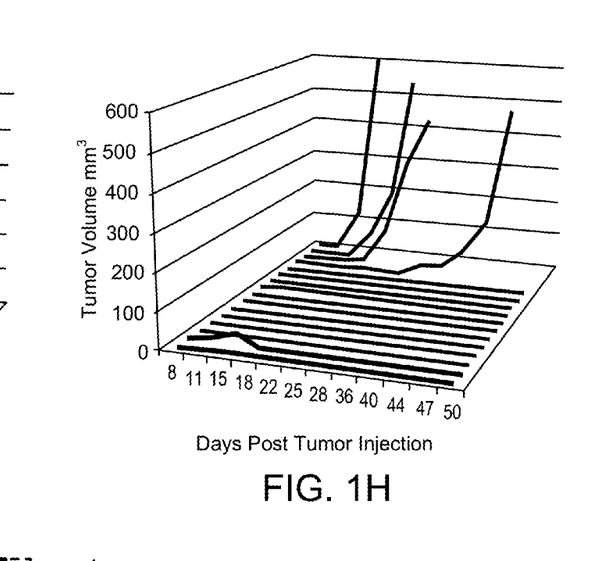
Figure 1I:
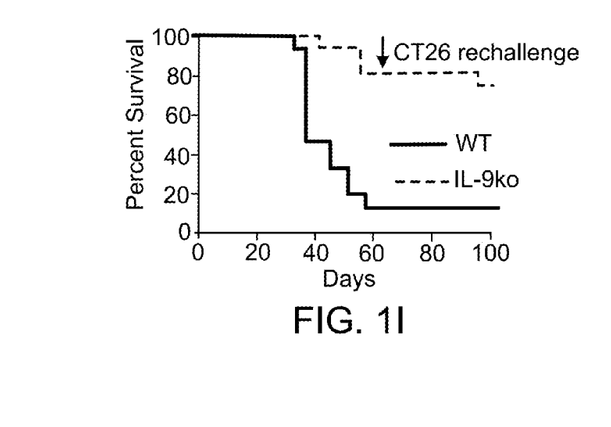

To investigate whether the tumor rejection seen in IL-9ko mice was confined to mammary carcinomas, the colon carcinoma cell line CT26 was injected into both WT (n=15) and IL-9ko mice (n=16). CT26 tumors developed in 87% (13/15) of WT mice (FIG. 1G), whereas tumors developed in only 25% (4/16) of IL-9ko mice injected (FIG. 1H). Once more, the tumors that developed in IL-9ko mice grew slower than those in WT mice, and 75% of IL-9ko mice remained tumor free 30 days after the initial challenge (p=0.001). At this point, ten IL-9ko and two WT mice were rechallenged with CT26 (FIG. 1I, arrow). No tumor growth was observed in ten IL-9ko mice and one WT mouse (CT26 tumor developed in the second WT mouse), again suggesting a memory response in IL-9ko mice.

Figure 2:
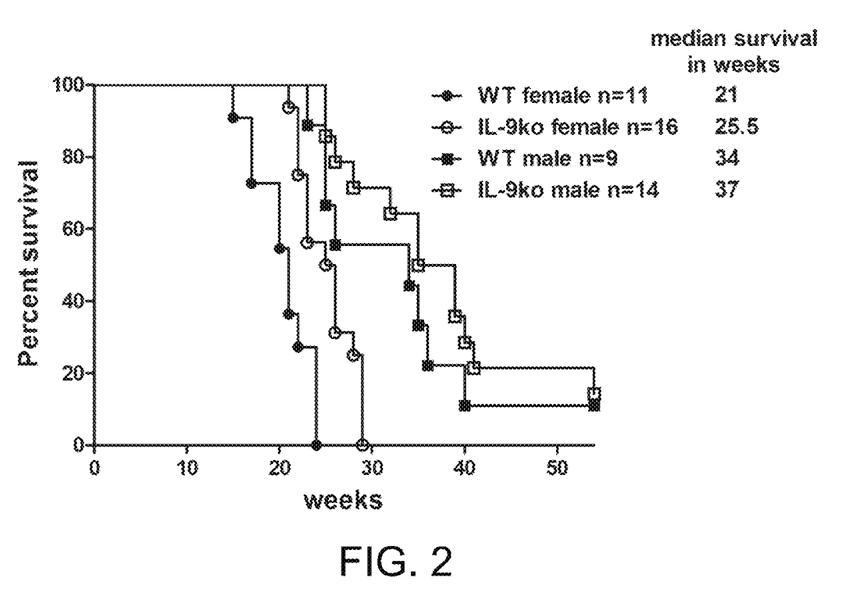
FIG. 2. Spontaneous, autochthonous mammary tumors appear by four months of age in female mice BALB/neuT mice (WT). Double transgenic IL-9ko/neuT mice were generated, and the appearance of autochthonous tumors as compared to WT/neuT mice was monitored. Autochthonous breast carcinoma tumors appeared significantly later in female IL-9 deficient neuT mice than in WT/neuT mice p=0.002. This suggests that IL-9 may have a role in tumor immunosurveillance.

IL-9 Deficiency Leads to Delayed Onset of Autochthonous Mammary Tumors in Her2/neu Transgenic Mice Double transgenic mice deficient in IL-9 and expressing activated Her2/neu were monitored from birth to track tumor onset and growth as compared to that of BALB/c/Her2/neu mice. Mice were sacrificed when one or more mammary tumors reached 10 $mm^2$, and their life span was recorded in weeks. A survival plot (FIG. 2) segregating males from females showed a significant increase in survival in females deficient in IL-9 (p=0.01).

T Cells are Essential for Tumor Rejection in IL-9Ko Mice

Figure 3A:
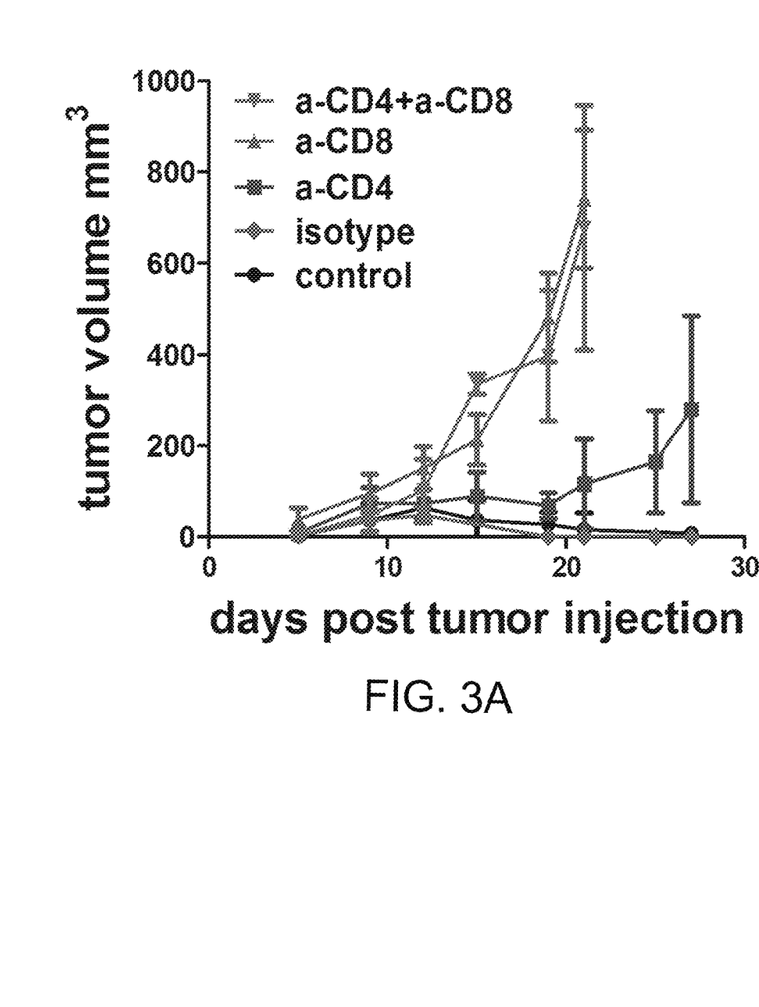
FIGS. 3A-C. $CD8^+$ T cells are essential for tumor rejection in IL-9ko mice. (A) Growth of $1 \times 10^6$ 4T1 cells implanted s.c. in the flank of IL9-ko mice treated with neutralizing antibodies against CD4, CD8, $CD4^+CD8$ or isotype control. There were 6-8 mice per cohort and data shown are cumulative of two separate experiments. (B) Average tumor sizes in each treatment cohort 21 days post tumor injection. (C) Depletion of $CD8^+$ T cells with anti-CD8 antibody in the IL-9ko mice that rejected 4T1 tumors from 2A. Arrows indicate dosage times once weekly for three weeks.
Figure 3B:
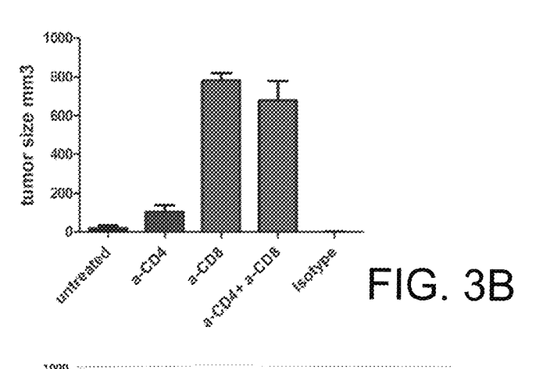

Evaluation of the immune composition of spleens and lymph nodes of 4T1 bearing WT and IL-9ko mice revealed increased total numbers of $CD4^+$ and $CD8^+$ T cells in IL-9ko mice, and a concomitant decrease in numbers of $CD11b^+$ $Gr1^+$ cells. However, closer scrutiny revealed that any difference in total numbers was directly related to tumor size and not to IL-9 status. Since tumor rejection occurred 10-14 days after tumor inoculation (FIG. 1E), timing that is reminiscent of an adaptive immune response, and that this resulted in a memory response, whether T cells were involved in tumor rejection in an IL-9 deficient context was evaluated. To test this, IL-9ko mice were inoculated with 4T1 tumors, and CD4$^+$ and CD8$^+$ T cells were depleted with mAb. Cohorts comprised 6-8 mice, and were treated as follows: anti-CD4, anti-CD8, both anti-CD4 and anti-CD8, isotype control antibody or untreated. Growth was monitored over 30 days. Both the untreated and isotype control antibody treated IL-9ko mice gave evidence of tumor rejection between days 10 and 14 post tumor injection, with rejection completed one week later. In contrast, CD8 depletion or joint CD4 and CD8 depletion resulted in 4T1 tumor growth indistinguishable from that observed in WT mice (FIG. 3A). Finally, depletion of only CD4$^+$ T cells also prevented 4T1 rejection, but with slower tumor outgrowth than CD8$^+$ depletion. These results demonstrate that in an IL-9 deficient milieu, both CD8$^+$ and CD4$^+$ T cells were involved in tumor eradication, and that neither subset alone was sufficient for cure. Tumor sizes were tabulated 21 days post tumor injection, and confirm that CD8$^+$ depletion resulted in large tumor (averaging 700 mm$^3$) whereas untreated or isotype treated mice harbored very small tumors (averaging 14 mm$^3$) or no tumors at all (FIG. 3B).

These results suggest that the presence of IL-9 negatively regulates T cell function within 10-14 days of tumor challenge. The precise source of IL-9 in the tumor microenvironment is yet to be determined. However, both 4T1 and TUBO cells do not transcribe either IL-9 or IL9R mRNA, nor do they secrete IL-9 in vitro, as measured by ELISA using supernatants of tumors generated in IL-9ko mice and cultured for 3 days.

Figure 3C:
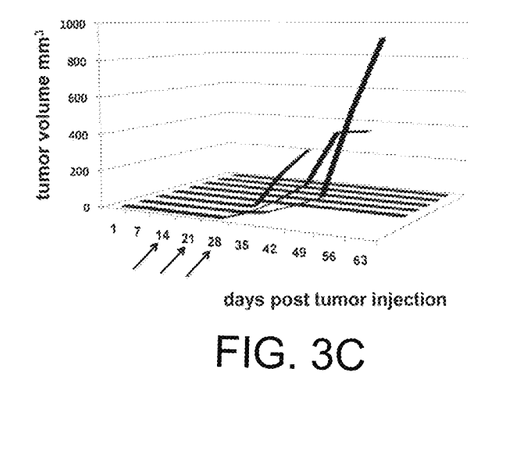

To test whether the absence of recurrent tumors in IL9ko 4T1 challenged mice reflected active T cell immunosurveillance, CD8$^+$ T cells were depleted in IL-9ko mice (n=8) that had rejected 4T1 cells 21 days prior (FIG. 3C, arrows). Tumors grew in 3/8 mice, and no tumor growth was evident in 5/8 mice. These data confirmed that active T cell surveillance was operative in at least a portion of non-recurrences, and raised the possibility that mice without tumor growth following CD8 depletion might harbor sufficient CD4$^+$ T cell immunologic memory to compensate for the CD8 depletion, or that the tumor was completely eradicated.

T Cells from IL-9Ko Mice are Activated and Tumor Specific

Figure 4A:
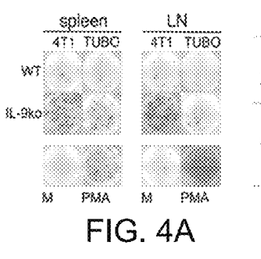
FIGS. 4A-E. $CD8^+$ T cells activated in a tumor specific manner and are tumor tropic. (A) ELISpot analysis measuring $IFN\gamma^+$ spots derived from total splenocytes (spleen) and lymphocytes (LN) from 4T1 bearing WT and IL-9ko mice. (B) Graph showing the average number of $IFN\gamma^+$ spots from triplicate wells. *asterisk indicates p=0.001. (C) $CD8^+$ T cells derived from naïve or tumor bearing WT and IL-9ko mice co-cultured with either 4T1 or BM185. Wells shown are representative of triplicate determinations from three biological replicates. (D) Graph showing the average numbers of $IFN\gamma^+$ spots in each well. Biological replicates are denoted as follows: WT naïve (WT N1-3), WT bearing 4T1 (WT TB1-3), IL-9ko naïve (IL9ko N1-3) and IL-9ko bearing 4T1 (IL9ko TB1-3). The *asterisk represents the significance of the difference in number of spots when comparing $CD8^+$ T cells from tumor bearing WT versus IL-9ko mice (p=0.007). Representative data of duplicate experiments with three mice in each condition. (E) Immunohistochemical evaluation of $CD8^+$ T cells present in 4T1 tumor derived from WT (lower panel) and IL-9ko (upper panel) mice. Each series is comprised of sequential slides to show morphology (H&E), anti-CD8 staining, and a negative control. Images are representative of three tumors from three individual mice in each strain. Bar represents 100 μm. M=media, PMA=Phorbol 12-myristate 13-acetate.
Figure 4B:
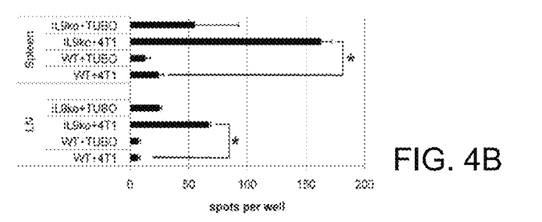

To confirm that tumor rejection was due to the sensitization of a tumor specific immune component, total splenocytes and lymphocytes (from tumor draining lymph nodes) were harvested from 4T1 bearing WT and IL-9ko mice 14 days after tumor injection. These cells were co-cultured with either 4T1 (target tumor) or TUBO (negative control tumor) cells to measure the number of cells that were activated in a tumor specific manner, using the number of IFNγ$^+$ spots as a reporter of activation (FIG. 4A). The number of IFNγ$^+$ spots present in WT co-cultured with 4T1 cells was near the levels of negative control (TUBO) tumor. In contrast, IL-9ko derived splenocytes and lymphocytes were activated in a tumor specific manner. Moreover, IL-9ko derived splenocytes (6.5 fold increase) and lymphocytes (9.7 fold increase) showed a significantly higher degree of activation in the presence of 4T1 as compared to WT cells (FIG. 4B, p=0.001).

Figure 4C:
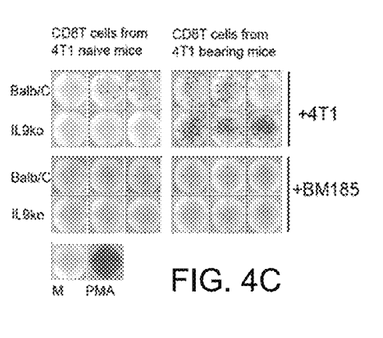
Figure 4D:
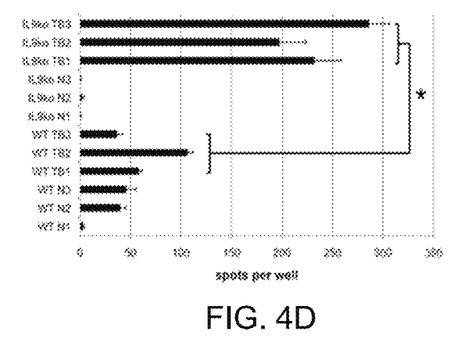

Since it was observed that T cell depletion resulted in tumor growth in IL-9ko mice, the ELISpot assay was repeated with isolated CD4$^+$ T cells and CD8$^+$ T cells. These cells were co-cultured with 4T1 or BM185 cells, a BALB/c background murine leukemia cell line used here as a negative control (FIG. 4C). Again using the number of IFNγ$^+$ spots as a reporter of T cell activation, a 3.6 fold increase in the number of activated CD8$^+$ T cells was found in the population derived from tumor bearing IL-9ko mice as compared to their WT counterparts: an average of 239 of IFNγ$^+$ spots in cells from IL-9ko mice, versus 67 spots in WT cells (FIG. 4D, p=0.007). Furthermore, activation of CD8$^+$ T cells was 4T1 specific, since there were no measurable IFNγ$^+$ spots when CD8$^+$ T cells were co-cultured with BM185 cells. Phorbol 12-myristate 13-acetate (PMA) was used as a positive control to confirm that the WT CD8$^+$ T cells were capable of activation. A similar experiment using CD8$^+$ T cells from TUBO bearing mice yielded similar results. CD4$^+$ T cells tested under identical conditions (T cells plus tumor cell lines in the absence of syngeneic antigen-presenting cells) produced IFNγ$^+$ spots only if exposed to PMA, consistent with an inability to recognize MHC Class II non-expressing tumor lines directly.

Figure 4E:
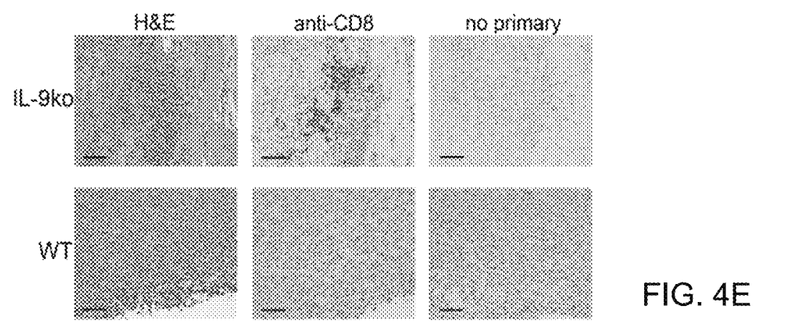

CD8$^+$ T Cells are Found in 4T1 Tumors Growing in IL-9Ko Mice, but not in Tumors Growing in WT Mice Having observed that CD8$^+$ T cells were key effectors in tumor eradication, and that they were activated in a tumor specific manner, it was sought to verify the presence of CD8$^+$ T cells in 4T1 tumors that were in the process of being rejected. WT and IL-9ko mice were injected with 4T1 cells, and tumor growth monitored. After 7 days, the tumors in WT mice were robustly growing (an average of 5 mm$^2$) (FIG. 1D), whereas tumors growing in IL-9ko mice were decreasing in size (2-3 mm$^2$) (FIG. 1E). Tumors were harvested at this point, formalin fixed, and paraffin embedded. Staining with anti-CD8 revealed a population of CD8$^+$ cells arranged mostly in groups at the margins of shrinking 4T1 tumors in the IL-9ko mice (FIG. 4E). No CD8$^+$ cells were observed in tumors growing in WT mice, even though the ELISpot analyses revealed 4T1-specific CD8$^+$ T cells in the spleens of WT 4T1-bearing mice (FIG. 4D).

Figure 5A:
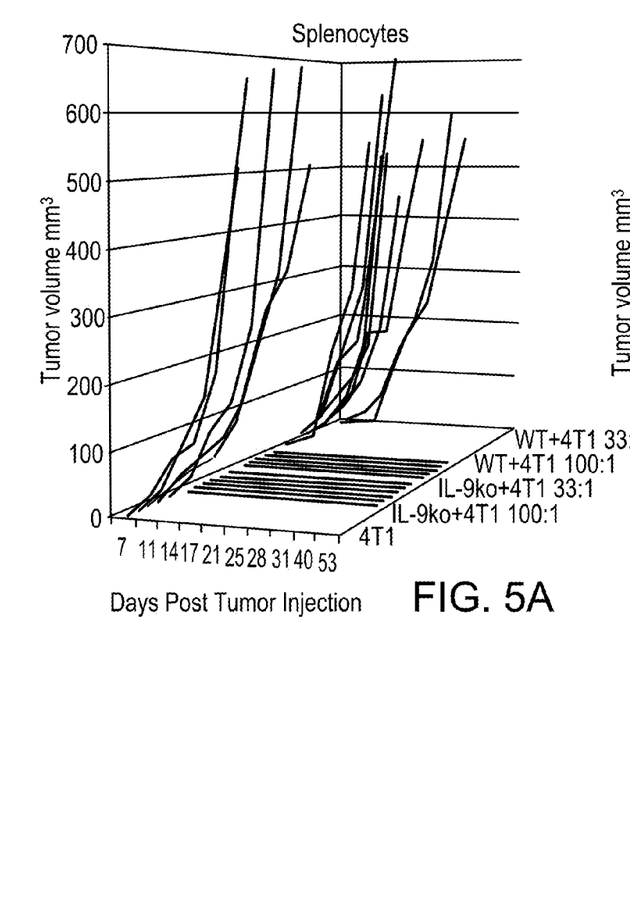
FIGS. 5A-B. Splenocytes, or $CD8^+$ T cells from IL-9ko mice that rejected 4T1 tumors, also impede 4T1 growth in WT mice. (A) Splenocytes derived from tumor bearing WT (WT+4T1) or IL-9ko (IL-9ko+4T1) mice were mixed with 4T1 cells and implanted s.c. in the flank of WT mice in the given ratios (100:1 and 33:1), holding the number of 4T1 cells constant at $2.5 \times 10^4$. Each line represents tumor growth in one mouse, and the cohorts are colored as follows: 1) 4T1 only, blue 2) IL-9ko+4T1 100:1, dark green 3) IL-9ko+4T1 33:1, light green 4) WT+4T1 100:1 purple and 5) WT+4T1 33:1, red. Shown is one of two determinations. (B) Enriched CD8+ T cells derived from either naïve or 4T1 tumor bearing, WT or IL-9ko mice were co-injected s.c. into WT mice in a ratio of 25:1. Each cohort contains duplicate mice injected with 4T1 and cells from three individual donor mice. Each line represents tumor growth in one mouse, and the cohort colors define the CD8+ T cell donor sub-sets as follows: 1) WT+4T1, dark blue 2) WT naïve, light blue 3) IL-9ko+4T1, dark green and 4) IL-9ko naïve, light green.
Figure 5B:
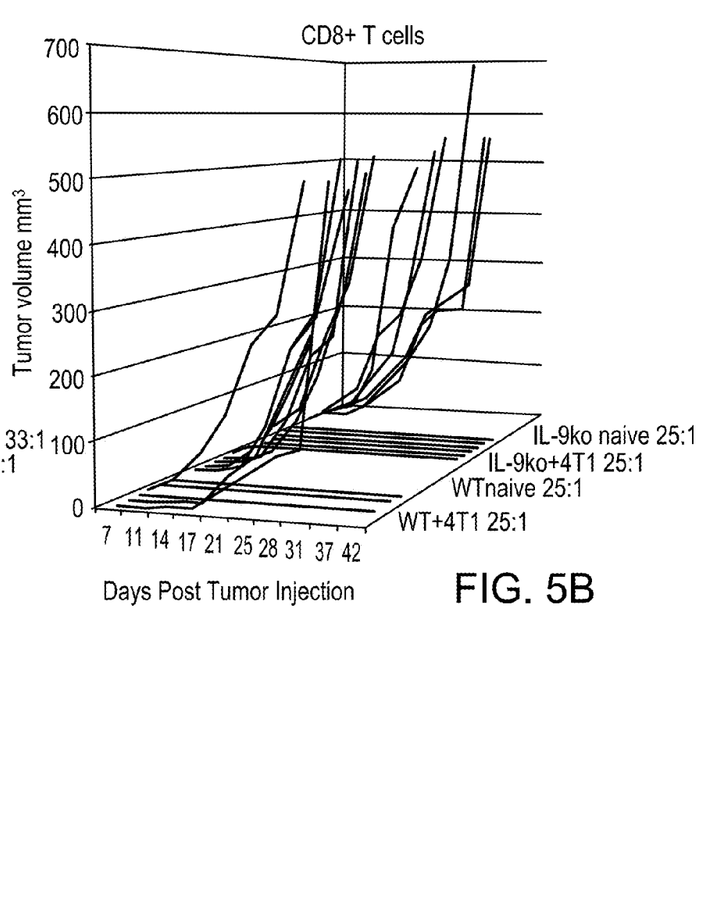

Splenocytes, or CD8$^+$ T Cells from IL-9Ko Mice that Rejected 4T1 Tumors, Also Abrogate 4T1 Growth in WT Mice Winn assays were employed to test whether activated splenocytes from IL-9ko mice that had rejected 4T1 tumors were capable of inducing tumor rejection in WT mice. IL-9ko mice that rejected 4T1 tumors were rechallenged with 4T1 cells to boost the levels of memory cells. Total splenocytes were then harvested from the rechallenged mice, and mixed with 4T1 cells prior to injection in the flank of WT mice. WT mice were segregated into 3 cohorts, which received increasing numbers of splenocytes, holding the number of tumor cells constant: 1) no splenocytes added, 2) 33:1, and 3) 100:1. Splenocytes from 4T1 bearing WT mice were used in the same proportions as a control. Tumor growth was monitored twice weekly, revealing tumor growth in WT mice that received only 4T1, and complete abrogation of tumor growth in all the mice that received IL-9ko activated splenocytes (FIG. 5A). Co-injection of 4T1 and splenocytes derived from 4T1 bearing WT mice grew similarly to the mice that received only 4T1. These results revealed that splenocytes derived from mice that had rejected 4T1 contained cells that were capable of eradicating 4T1 tumor cells in a WT context.

The experiment was repeated with negatively isolated CD8$^+$ T cells to verify the finding that depletion of CD8$^+$ T cells enables tumor growth in IL-9ko mice (FIG. 3A). CD8$^+$ T cells were harvested from spleens of the following groups of mice: 1) WT bearing 4T1 tumors, 2) naïve WT, 3) IL-9ko bearing 4T1 tumors, and 4) naïve IL-9ko. CD8$^+$ T cells were mixed with 4T1 cells in a ratio of 25:1, injected into WT mice, and tumor growth was monitored. As observed before (FIG. 5A), cells derived from tumor bearing IL-9ko mice prevented 4T1 growth in 6/6 mice. Cells isolated from both IL-9ko and WT naïve mice permitted 4T1 growth. Surprisingly, half of the mice treated with CD8+ T cells from tumor bearing WT mice prevented tumor growth, and half enabled tumor growth. These findings confirm the observations from the ELISpot assays (FIG. 3C), which revealed that CD8+ T cells derived from IL-9ko mice have 3.6 fold more tumor reactive cells than their WT equivalents.

Anti-IL-9 Treatment Results in Slowed Tumor Growth in WT Mice

Figure 6A:
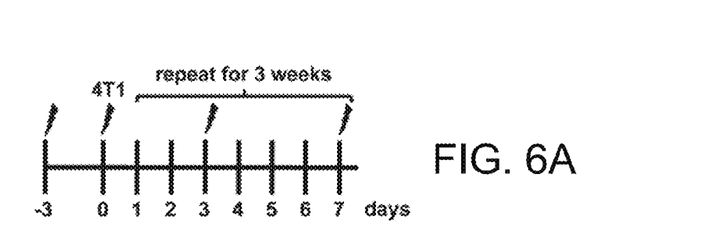
FIGS. 6A-B. Anti-IL-9 treatment results in slowed tumor growth in WT mice. (A) Representation of the treatment schedule to measure the effect of IL-9 depletion on tumor growth. Symbols mark the days of anti-IL-9 injections, twice a week for 3 weeks (3X). $2.5 \times 10^4$ 4T1 cells were injected on day 0. (B) Box-whisker plot of tumor growth in 3 cohorts of mice: untreated (white boxes, n=7), isotype control antibody (dotted boxes, n=8) and anti-IL-9 antibody (checkered boxes, n=11). Each box contains a line representing the median, and is bounded by the upper and lower quartiles. Minimum and maximum values are shown as whiskers. The bar frames the period of time (days 0 to 15) during which there is a significant difference in growth between the isotype control and anti-IL-9 treated cohorts (*asterisk, p=0.03). Data is cumulative of two independent experiments.
Figure 6B:
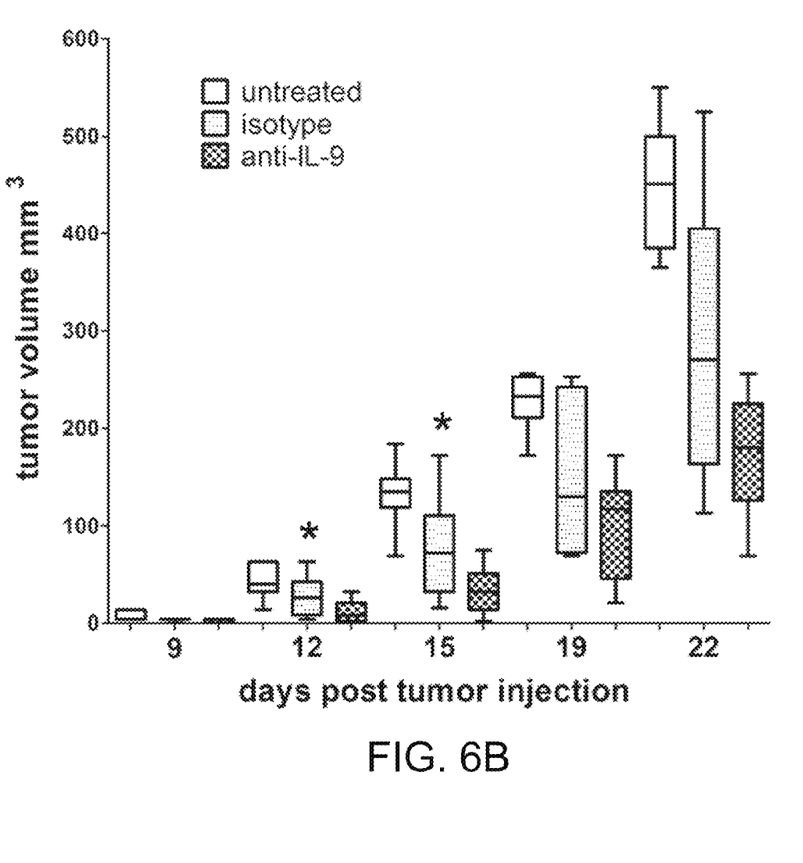

If IL-9 is an important factor in tumor development, then neutralizing IL-9 in WT mice with nascent 4T1 should lead to slowed tumor growth or tumor rejection. WT mice were inoculated with 4T1 cells and separated into three cohorts: 1) untreated, 2) treated with neutralizing anti-IL-9, and 3) treated with isotype control (FIG. 6A), and tumor growth was monitored. Mice treated with anti-IL-9 antibody exhibited significant delay in tumor growth (days 0-15) as compared to untreated mice ($p<0.0001$), and also when compared to isotype control antibody (FIG. 6B, $p=0.03$). The difference in growth between anti-IL-9 and untreated remained highly significant throughout the three weeks ($p<0.0001$). However, due to the high degree of variation in the isotype control cohort there was no measurable significance in 4T1 growth in latter time points.

IL-9 Deficiency Prevents the Establishment of 4T1 Tumor Foci in the Lung

Figure 7A:
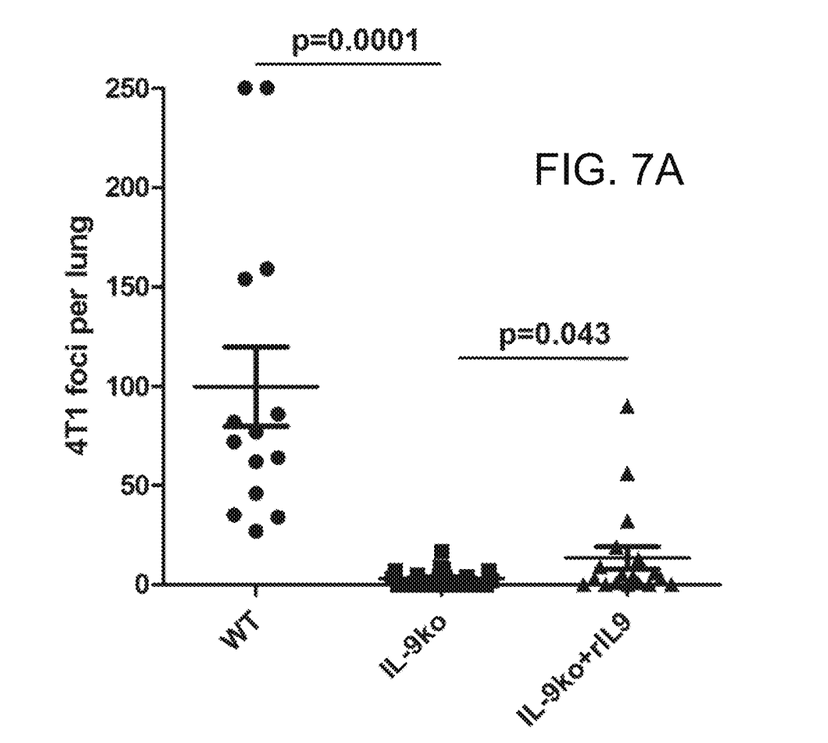
FIGS. 7A-B. IL-9 deficiency prevents experimental 4T1 metastasis growth in the lung, whereas addition of recombinant IL-9 eliminates the protective quality of IL-9 deficiency. (A) 4T1 breast carcinoma cells were injected in the tail vein of WT and IL-9ko mice. The number of macroscopic tumors from each lung are shown. Cross bars indicate the median number of metastases, and bounding bars represent upper and lower quartiles. (B) Representative images of 4T1 foci in lungs from each treatment group. IL-9 deficiency led to a significantly reduction in number of lung lesions, suggesting that IL-9 contributes to the seeding or survival of circulating tumor cells.
Figure 7B:
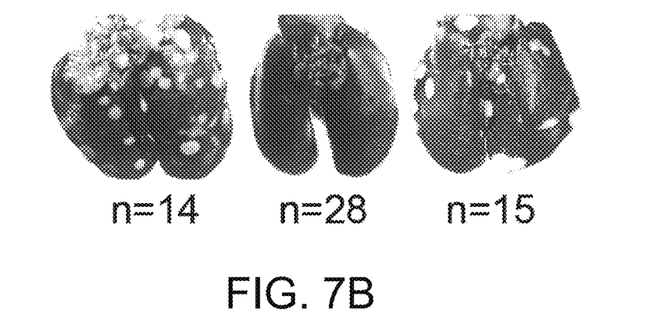

Since few IL-9ko mice that developed 4T1 tumors never had evidence of macro metastases in the lungs, an experimental metastasis model was used to verify whether IL-9 plays a role in 4T1 seeding in the lung. Tail vein injections of $1\times10^5$ 4T1 cells led to metastatic lesions in WT mice (an average of 87 foci per lung), whereas the majority of IL-9ko mice did not develop visible metastases (an average of 3 foci per lung, $p=0.0001$) (FIGS. 7A and 7B). Addition of recombinant IL-9 led to enhanced 4T1 seeding in the lungs of IL-9ko mice (an average of 13 foci per lung) ($p=0.043$, FIGS. 7A and 7B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having colon or breast cancer, wherein said method comprises administering, to said mammal, a therapeutically effective amount of an agent and an inhibitor of IL-9 signaling, wherein said agent is selected from the group consisting of an anti-PD-1 agent, an anti-PD-L1 agent, an anti-CTLA4 agent, trastuzumab, cyclophosphamide, gemcitabine, capecitabine, azacytadine, bortezomib, carboplatin, cisplatin, etoposide, imatinib, 5-fluorouracil, docetaxel, paclitaxel, nab-paclitaxel, irinotecan, doxorubicin, methotrexate, and oxaliplatin, wherein said inhibitor comprises an anti-IL-9 or anti-IL-9 receptor antibody, and wherein the progression of said colon or breast cancer or the number of colon or breast cancer cells within said mammal is reduced.

2. The method of claim 1, wherein said mammal is a human.

3. The method of claim 1, wherein said method comprises administering said agent to said mammal before said inhibitor is administered to said mammal.

4. The method of claim 1, wherein said method comprises administering said agent to said mammal at least one month before said inhibitor is administered to said mammal.

5. The method of claim 1, wherein said method comprises administering said agent to said mammal at least two months before said inhibitor is administered to said mammal.

* * * * *

UNITED STATES PATENT AND TRADEMARK OFFICE
CERTIFICATE OF CORRECTION

PATENT NO. : 9,833,512 B2  
APPLICATION NO. : 14/682493  
DATED : December 5, 2017  
INVENTOR(S) : Dominique B. Hoelzinger et al.

Page 1 of 1

It is certified that error appears in the above-identified patent and that said Letters Patent is hereby corrected as shown below:

On the Title Page

Column 2, item (57) Abstract, delete "anti-IL9" and insert -- anti-IL-9 --, therefor.

In the Claims

Column 14, Line 20, Claim 1, delete "azacytadine," and insert -- azacytidine, --, therefor.

Signed and Sealed this  
Thirtieth Day of July, 2019

Andrei Iancu  
*Director of the United States Patent and Trademark Office*